US010080535B2

(12) United States Patent
Kyllonen et al.

(10) Patent No.: US 10,080,535 B2
(45) Date of Patent: *Sep. 25, 2018

(54) IMAGE PLATE READOUT DEVICE (71) Applicant: PaloDEx Group Oy, Tuusula (FI)

(72) Inventors: Mika Kyllonen, Helsinki (FI); Jari Taskinen, Tuusula (FI)

(73) Assignee: PaloDEx Group Oy, Tuusula (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,594

(22) Filed: Apr. 25, 2017

(65) Prior Publication Data
US 2017/0224297 A1    Aug. 10, 2017

Related U.S. Application Data

(63) Continuation of application No. 14/721,663, filed on May 26, 2015, now Pat. No. 9,665,752, which is a
(Continued)

(30) Foreign Application Priority Data

Dec. 23, 2008    (FI) .................................... 20086241

(51) Int. Cl.
*A61B 6/00* (2006.01)
*H04N 1/00* (2006.01)
*A61B 6/14* (2006.01)

(52) U.S. Cl.
CPC .............. *A61B 6/4423* (2013.01); *A61B 6/00* (2013.01); *A61B 6/14* (2013.01); *A61B 6/4216* (2013.01);
(Continued)

(58) Field of Classification Search
CPC .... A61B 6/00; A61B 6/14; A61B 6/46; A61B 6/4216; A61B 6/4423
See application file for complete search history.

(56) References Cited

U.S. PATENT DOCUMENTS 3,495,149 A    2/1970 Swain
3,901,607 A    8/1975 Kingsland
(Continued)

FOREIGN PATENT DOCUMENTS

EP    1640800    3/2006
EP    2128697    12/2009
(Continued)

OTHER PUBLICATIONS

Communication dated May 7, 2010 and European Search Opinion and European Search Report dated Apr. 28, 2010, received in corresponding European Patent Application No. 09180462.5.
(Continued)

*Primary Examiner* — Andrew Bee
(74) *Attorney, Agent, or Firm* — Andrus Intellectual Property Law, LLP (57) ABSTRACT

The invention relates to an image plate readout device, the readout device comprising receiver elements for the reception of an image plate and/or a transfer element intended for an image plate. In connection with the readout device is provided, for detecting an object, at least one sensing element, which is in turn set in data communication with the readout device in such a way that, upon detecting an object, the sensing element delivers a signal to the readout device. In response to being triggered by a signal delivered by the sensing element, the readout device executes some function.

27 Claims, 1 Drawing Sheet

Related U.S. Application Data continuation of application No. 12/642,389, filed on Dec. 18, 2009, now Pat. No. 9,066,648.

(52) U.S. Cl.
CPC ............... *A61B 6/46* (2013.01); *A61B 6/467* (2013.01); *H04N 1/00251* (2013.01); *H04N 1/00267* (2013.01); *H04N 1/00381* (2013.01); *H04N 2201/0079* (2013.01); *H04N 2201/0081* (2013.01)

(56) References Cited

U.S. PATENT DOCUMENTS

| | | | |
|---|---|---|---|
| 3,970,844 A | 7/1976 | Fenn et al. | |
| 4,096,391 A | 6/1978 | Barnes | |
| 4,176,275 A | 11/1979 | Korn et al. | |
| 4,236,078 A | 11/1980 | Kotera et al. | |
| 4,239,968 A | 12/1980 | Kotera et al. | |
| 4,316,666 A | 2/1982 | Ceelen | |
| 4,320,296 A | 3/1982 | Ishida et al. | |
| 4,327,422 A | 4/1982 | Imazeki et al. | |
| 4,346,295 A | 8/1982 | Tanaka et al. | |
| 4,346,983 A | 8/1982 | Jeromin et al. | |
| 4,387,428 A | 6/1983 | Ishida et al. | |
| 4,394,581 A | 7/1983 | Takahashi et al. | |
| 4,453,162 A | 6/1984 | Money et al. | |
| 4,462,113 A | 7/1984 | Iwata | |
| 4,472,822 A | 9/1984 | Swift | |
| 4,485,302 A | 11/1984 | Tanaka et al. | |
| 4,496,973 A | 1/1985 | Horikawa et al. | |
| 4,498,005 A | 2/1985 | Oono et al. | |
| 4,498,006 A | 2/1985 | Horikawa et al. | |
| 4,527,060 A | 7/1985 | Suzuki et al. | |
| 4,527,061 A | 7/1985 | Horikawa et al. | |
| 4,547,665 A | 10/1985 | Little et al. | |
| 4,564,760 A | 1/1986 | Noguchi et al. | |
| 4,568,832 A | 2/1986 | Tanaka et al. | |
| 4,583,489 A | 4/1986 | Thourson et al. | |
| 4,584,483 A | 4/1986 | Kato | |
| 4,590,517 A | 5/1986 | Kato et al. | |
| 4,654,760 A | 3/1987 | Matheson et al. | |
| 4,710,626 A | 12/1987 | Takahashi et al. | |
| 4,739,480 A | 4/1988 | Oono et al. | |
| 4,777,597 A | 10/1988 | Shiraishi et al. | |
| 4,814,618 A | 3/1989 | Saito et al. | |
| 4,816,676 A | 3/1989 | Aagano | |
| 4,816,677 A | 3/1989 | Adachi et al. | |
| 4,816,690 A | 3/1989 | Adachi et al. | |
| 4,877,958 A | 10/1989 | Agano et al. | |
| 4,880,987 A | 11/1989 | Hosoi et al. | |
| 4,888,695 A | 12/1989 | Shiraishi et al. | |
| 4,904,868 A | 2/1990 | Kohda et al. | |
| 4,943,723 A | 7/1990 | Adachi et al. | |
| 4,960,994 A | 10/1990 | Muller et al. | |
| 4,983,834 A | 1/1991 | Lindmayer et al. | |
| 5,073,916 A | 12/1991 | Mirlieb et al. | |
| 5,168,160 A | 12/1992 | Jeromin et al. | |
| 5,272,339 A | 12/1993 | Shimura et al. | |
| 5,315,444 A | 5/1994 | Ishiguro et al. | |
| 5,334,831 A | 8/1994 | Maurice | |
| 5,335,664 A | 8/1994 | Nagashima | |
| 5,440,146 A | 8/1995 | Steffen et al. | |
| 5,677,940 A | 10/1997 | Suzuki et al. | |
| 5,686,882 A | 11/1997 | Giani | |
| 5,801,391 A | 9/1998 | Arakawa et al. | |
| 5,812,266 A | 9/1998 | Hercher | |
| 5,852,301 A | 12/1998 | Niimura et al. | |
| 5,900,640 A | 5/1999 | Ogura | |
| 5,923,856 A | 7/1999 | Hazama et al. | |
| 5,932,982 A | 8/1999 | Pezzelli, Jr. | |
| 5,981,953 A | 11/1999 | Schoeters | |
| 6,023,071 A | 2/2000 | Ogura et al. | |
| 6,044,131 A | 3/2000 | McEvoy et al. | |
| 6,130,440 A | 10/2000 | Ogura | |
| 6,175,610 B1 | 1/2001 | Peter | |
| 6,197,117 B1* | 3/2001 | Li | H01L 21/681 118/715 |
| 6,236,058 B1 | 5/2001 | Ikami | |
| 6,256,405 B1 | 7/2001 | Some et al. | |
| 6,315,444 B1 | 11/2001 | Koren | |
| 6,376,857 B1 | 4/2002 | Imai | |
| 6,469,312 B2 | 10/2002 | Agano | |
| 6,528,813 B2 | 3/2003 | Yasuda | |
| 6,583,630 B2 | 6/2003 | Mendes et al. | |
| 6,680,483 B2 | 1/2004 | Shoji | |
| 6,737,970 B2 | 5/2004 | Wuestefeld et al. | |
| 6,759,673 B2 | 7/2004 | Akimoto et al. | |
| 6,936,829 B2 | 8/2005 | Nishioka | |
| 7,148,501 B1 | 12/2006 | Kralles et al. | |
| 7,164,344 B2 | 1/2007 | Deguchi et al. | |
| 7,195,645 B2 | 3/2007 | Disilvestro et al. | |
| 7,211,818 B2 | 5/2007 | Imai et al. | |
| 7,212,283 B2 | 5/2007 | Hother et al. | |
| 7,227,117 B1 | 6/2007 | Lackemann et al. | |
| 7,227,924 B2 | 6/2007 | Zhou et al. | |
| 7,245,211 B2 | 7/2007 | Ota | |
| 7,308,614 B2 | 12/2007 | Kojori | |
| 7,420,197 B2 | 9/2008 | Irisawa | |
| 7,492,250 B2 | 2/2009 | Yoshida et al. | |
| 7,531,822 B1 | 5/2009 | Minnigh et al. | |
| 7,570,064 B2 | 8/2009 | Roziere | |
| 7,583,930 B2 | 9/2009 | Minotani et al. | |
| 7,767,981 B2 | 8/2010 | Kuwabara et al. | |
| 7,782,192 B2 | 8/2010 | Jeckelmann et al. | |
| 7,889,843 B2 | 2/2011 | Watanabe | |
| 7,991,119 B2 | 8/2011 | Yoshida et al. | |
| 8,053,737 B2 | 11/2011 | Ohta et al. | |
| 8,077,601 B2 | 12/2011 | Maze et al. | |
| 2001/0010541 A1 | 8/2001 | Fernandez et al. | |
| 2001/0021243 A1 | 9/2001 | Yano | |
| 2001/0032945 A1 | 10/2001 | Yasuda | |
| 2002/0043636 A1 | 4/2002 | Kimura | |
| 2002/0060303 A1 | 5/2002 | Yonekawa et al. | |
| 2002/0070860 A1 | 6/2002 | Wuestefeld | |
| 2002/0105427 A1 | 8/2002 | Hamamoto et al. | |
| 2003/0080868 A1 | 5/2003 | Nelson | |
| 2004/0028174 A1 | 2/2004 | Koren | |
| 2004/0066278 A1 | 4/2004 | Hughes et al. | |
| 2004/0066279 A1 | 4/2004 | Hughes et al. | |
| 2004/0094711 A1 | 5/2004 | Lee | |
| 2004/0094731 A1 | 5/2004 | Arakawa | |
| 2004/0211894 A1 | 10/2004 | Hither | |
| 2004/0234032 A1 | 11/2004 | Nokita | |
| 2005/0025706 A1 | 2/2005 | Kagermeier | |
| 2005/0078793 A1 | 4/2005 | Ikeda | |
| 2005/0218356 A1 | 10/2005 | Apajasaari | |
| 2005/0226361 A1 | 10/2005 | Zhou et al. | |
| 2005/0247898 A1 | 11/2005 | Yonekawa et al. | |
| 2006/0113500 A1 | 6/2006 | Auer et al. | |
| 2006/0149167 A1 | 7/2006 | Yeh et al. | |
| 2006/0271199 A1 | 11/2006 | Johnson | |
| 2007/0086911 A1 | 4/2007 | Yamazaki et al. | |
| 2007/0130547 A1 | 6/2007 | Boillot | |
| 2008/0061964 A1 | 3/2008 | Yoshida et al. | |
| 2008/0085228 A1 | 4/2008 | Yamazaki et al. | |
| 2008/0129486 A1 | 6/2008 | Jeckelmann et al. | |
| 2008/0253519 A1 | 10/2008 | Bonfiglio et al. | |
| 2008/0306379 A1 | 12/2008 | Ikuma et al. | |
| 2009/0177109 A1 | 7/2009 | Yeh et al. | |
| 2009/0302220 A1 | 12/2009 | Micko | |
| 2009/0309704 A1 | 12/2009 | Chang et al. | |
| 2010/0097830 A1 | 4/2010 | Wang | |
| 2010/0191055 A1 | 7/2010 | Minai et al. | |
| 2010/0320973 A1 | 12/2010 | Nishida | |
| 2011/0225478 A1 | 9/2011 | Kimura | |

FOREIGN PATENT DOCUMENTS

| | | |
|---|---|---|
| FI | 92633 | 8/1994 |
| FR | 2652564 | 4/1991 |
| JP | 36053 | 1/1991 |
| JP | 05225767 | 9/1993 |
| JP | 2004264609 | 9/2004 |

(56) References Cited

FOREIGN PATENT DOCUMENTS

| JP | 2004283365 | 10/2004 |
|----|------------|---------|
| JP | 2006263609 | 10/2006 |
| JP | 2008268837 | 11/2008 |
| JP | 2008301970 | 12/2008 |
| JP | 2004264604 | 9/2009 |

OTHER PUBLICATIONS

Opposition filed in corresponding European Patent Application No. 09180462.5, dated Apr. 23, 2012.
Communication of a Notice of Opposition received in corresponding European Patent Application No. 09180462.5, dated May 7, 2012.
European Search Report for corresponding application EP 12 19 0509, having a completion date of Nov. 20, 2012.
Notice of Office Action issued in corresponding Korean Patent Application No. 0130132/2009, transmitted Oct. 24, 2013.
Communication from OKABE International Patent Office dated Nov. 22, 2013, referencing Office Action issued in Japanese Patent Application No. 2009-290748.
Notification of Reasons for Refusal issued from Japanese Patent Office dated Dec. 26, 2013 in Japanese Application No. 2009-290738.
Notification of Reasons for Refusal issued from Japanese Patent Office dated May 13, 2014 in Japanese Application No. 2009-290748.

\* cited by examiner

IMAGE PLATE READOUT DEVICE

CROSS-REFERENCE TO RELATED APPLICATIONS

This application is a continuation of U.S. application Ser. No. 14/721,663, filed May 26, 2015, which application was published on Nov. 12, 2015, as U.S. Publication No. US20150324620, which application is a continuation of U.S. application Ser. No. 12/642,389, filed Dec. 18, 2009, which application was published on Jun. 24, 2010, as U.S. Publication No. US20100156590, which application claims priority to Finish Application No. 20086241, filed Dec. 23, 2008, the contents of which are incorporated herein by reference in their entireties.

The invention relates to the concept of hygiene, involving for example image plates used in medical imaging processes, and instruments and installations, for example image plate readers, associated therewith. Specifically, the present invention relates to a method of operating an image plate readout device in a non-contacting manner or with minimal contact, as well as to such an image plate readout device.

PRIOR ART

The imaging media employed today in medical imaging processes include a traditional film, a reusable image plate, or an X-radiation monitoring wireless or wired sensor. In the event that a film is used, the film has been accommodated for example in a separate cassette protecting the film from visible light, which cassette may be in contact with a patient and his/her body fluids during radiography. Likewise, the image plate is shielded inside a protection device during radiography, the X-ray image being captured by placing the object to be imaged, for example a patient or part of a patient, between the source of X-radiation and the image plate contained within the protection device. Hence, the image plate protection device may come to contact with a patient and his/her body fluids during an imaging process, such as for example in intraoral radiography, during which the image plate shielded by a protection device is in the patient's mouth.

No matter which of the foregoing imaging media is employed, there is always a risk that disease carriers, originating from a patient and/or medical staff, may migrate to other patients and/or medical staff by way of the imaging medium. In the case of an image plate, for example, the first risk appears as early as in the packaging stage of an image plate, wherein the image plate is inserted for example in a protective cardboard or the like, and then, while accommodated in the protective cardboard or the like, in a shielding device, for example in a sealable hygienic shielding bag, ending up in contact e.g. with a patient during radiography. In the packaging process, an image plate, prior to being inserted in protection devices, may be contaminated e.g. by a packing person, for example by dropping the image plate on the floor or by touching it with bare hands or dirty gloves.

Another risk factor involves the poor liquid tightness of protection devices, for example a shielding bag, whereby, e.g. in intraoral radiography, a patient's body fluids may end up inside the shielding bag and proceed to contaminate an image plate contained in the shielding bag. Another risk with non-resistive shielding bags is that disease carriers, possibly inside the shielding bag, may migrate from within the shielding bag into a patient's mouth during radiography.

Still another risk is that the shielding bag is picked up from a patient's mouth for example by a nurse, who then brings the same instruments in contact with other objects, for example readout devices or structural elements or even other shielding bags, whereby disease carriers may pass from the nurse to other protection devices and, in the case of non-resistive shielding bags, even all the way to image plates.

There is a still further risk of disease carriers proceeding from an image plate to instruments in contact with the image plate, for example to readout device conveyor mechanisms, receiver elements or transfer elements, or to an outlet for image plates, or to a tray into which the read-out image plates return from the readout device, and further thereby to other image plates or persons or elements handling the same.

Prior known are a few solutions for improving the hygiene of, for example, intraoral image plates and instruments and installations associated therewith.

For example, the publication FI 92633 discloses one solution for protecting an intraoral image plate by means of two shielding bags, wherein the image plate is first inserted in an inner shielding bag open at one end, and which inner shielding bag is then inserted into an outer shielding bag, said outer shielding bag being intended to prevent a patient's saliva from proceeding, along with the inner bag, to a readout device, as well as to protect the patient from disease carriers possibly settled on the image plate surface. The image plate can be placed first in a cardboard cover and then in an outer shielding bag. In addition, the publication U.S. Pat. No. 6,315,444 also discloses a solution for protecting an imaging plate by means of an envelope type container, wherein the imaging plate is inserted in the envelope type container by way of a first end of the container for the duration of a radiographic procedure and is removed from a second end of the container after the radiographic procedure.

However, the above-cited solutions involve a few problems, for example a shielding bag opening process with uncontrolled tearing of the shielding bag. This involves a hazard that, in the process of opening a shielding bag, an image plate present inside the shielding bag is dropped, for example, on the floor or some other contaminating surface, whereby disease carriers may end up in contact with the image plate. The envelope type container described in U.S. Pat. No. 6,315,444 is in turn quite complicated in terms of its structure and manufacturing, because therein the point of inserting an image plate into the container is not the same as that of its extraction. Such a container is quite vulnerable to leaks as it includes several openings for the insertion or extraction of an image plate.

Still additionally, the solutions presented in either of the cited publications are not resistive as both are left with a flow-permitting passage in a folded joint established by a foldable flap, which allows a flow of liquid even all the way to contact with an opening intended for the insertion of an image plate, and thence further inside the container and to contact with the image plate. Moreover, for example the envelope type container presented in U.S. Pat. No. 6,315,444 is left with sharp corners as the flap is folded shut. First of all, such sharp corners feel uncomfortable in a patient's mouth, but there is also a hygiene risk as a sharp corner may cause further damage to a patient's mucous membranes and thereby facilitate the transfer of disease carriers to or from the patient's body.

Prior known are also a few solutions for the cleaning of contaminated intraoral image plates. For example, the publication US 2007/0086911 discloses a solution relating to disinfection, wherein the image plate readout device comprises a special disinfecting unit performing the disinfection by means of a thermal treatment, UV radiation, chemicals, or a gas treatment.

A problem in the solution presented in US 2007/0086911 is, however, the fact that the device explicitly disinfects image plates presently contained within an image plate readout device. In the event that a traditional image plate is disinfected for example by means of UV radiation, the image plate must be subjected thereafter to an erasing procedure or at least to a dark treatment prior to its reuse, which claims time and resources with at least one operation added to the process, and secondly, the image plate is not immediately reusable. In addition, powerful UV radiation is harmful to the image plate and shortens its service life.

SUMMARY

It is an objective of the invention to set aside drawbacks associated with the prior art. According to one embodiment, the invention pursues to improve the hygiene of image plates used in medical imaging processes, as well as that of instruments and installations, for example image plate readers, involved therein, and thereby to minimize the spreading of disease carriers by way of radiography-related media and/or medical staff amongst patients and/or medical staff members.

The objectives of the invention are achieved by an image plate readout device according to claim 1, as well as by a method according to claim 9 for operating such a readout device.

The image plate readout device of the invention is characterized by what is presented in claim 1 directed to a readout device.

In addition, the method of the invention for operating an image plate readout device is characterized by what is presented in claim 9 directed to a method.

The concepts presented in this document are used e.g. in the following meanings:

"The object of detection" is for example an operator of the readout device, an image plate, a protection device relevant to the image plate, a transfer element, or an identifier relevant to any of the above, for example an RFID identifier or a bar code. What can be detected about the operator is for example the proximity of the operator in the vicinity of a readout device or for example a gesture or a motion made by the operator, the term subsequently used for these being a gesture in order to simplify the text. The gesture can be for example a circle, a line or some other figure drawn in the air by a finger, which is detected by a sensing element. On the basis of a detected gesture, the readout device is adapted to execute a specific function, for example cleaning the installation or receiving and reading the image plate.

"The sensing element" is an element set in connection with the readout device and in data communication therewith, which senses an object of detection. The sensing element can be implemented for example by means of an infrared sensor, a thermal sensor, an RFID sensor, a photocell, a laser rangefinder, a capacitive sensor and/or a resistive sensor. According to one embodiment, the sensing element can also be a radar or a camera, enabling a detection of gestures and/or motions when the object of detection is for example an operator. In addition, the sensing element can be adapted to detect whether the object spends time in the vicinity of a readout device, for example longer than some specific preset time. The sensing element can be further adapted to detect whether the object returns to the vicinity of a readout device within a preset time span after the previous time that the sensing element has detected the object in its proximity. On the other hand, the sensing element can be adapted to detect some specific gesture and/or motion of the object, for example within some specific preset time period after the sensing element has detected the object in its proximity. The sensing element can be or can have associated therewith a mechanical element, for example a switch, which is adapted to mechanically detect for example a cassette or a transfer element for example at the inlet of a readout device, in the adapter, or in the immediate proximity of the adapter.

"The conveyor mechanism" is a mechanism, which conveys or otherwise carries an image plate or a transfer element (either with or without the image plate), inserted in a readout device, at least over part of the way inside the readout device, in order to be read for example by a reader unit of the readout device. The conveyor mechanism can be a mechanism consisting for example of conveyor belts, a carrier arm, a holder, rollers and/or guides or the like. According to one embodiment, the carrier arm or the image plate holder can be the same as a gripper element serving as the receiver element, the gripper element being adapted not only to receive an image plate or a transfer element, but also to carry the image plate or the transfer element within the readout device. In some embodiments, the conveyor mechanism is also adapted to carry an image plate or a transfer element to an outlet for image plates, which can be a separate outlet or co-function as an inlet, depending on the design of a readout device.

"The receiver element" is for example an element set in the immediate vicinity of a readout device for the reception of an image plate, or a transfer element intended for the image plate, in the readout device. The receiver element can be for example an adapter provided in connection with the conveyor mechanism, enabling image plates or transfer elements for image plates of various sizes to be fed into the readout device. The activation of a receiver element may comprise, for example, activating a set of instruments associated with the inlet of a readout device for enabling the placement of an image plate in said inlet either as such or fitted in a transfer element, for example adjusting an adapter as required by the image plate or the transfer element. According to one embodiment, the adapter may adjust itself for example as required by a transfer element, for example a cassette, in such a way that the transfer element, for example a cassette, remains in the adapter, and an imaging medium present inside the transfer element is passed from the adapter to the readout device for reading, thus also enabling a part of the transfer element remaining in the adapter, as well as the adapter itself, to be disinfected. The activation of a receiver element may also comprise switching the readout device's gripper element to a standby mode, enabling the placement of an image plate in the gripper element either as such or fitted in a transfer element. The receiver element can also be set in an offering condition, in which the image plate is left in the inlet of a readout device to be picked up by the operator. The receiver element may also be a protective lid of the readout device, which opens upon its activation.

"The transfer element" is for example an element, in which an image plate, used e.g. in intraoral radiography, is carried from place to place. The image plate within said transfer element can also be fed into a readout device to be carried by the readout device's conveyor mechanism and further to be read by the readout device's reader elements, and further to an outlet for read-out image plates. The outlet can be a separate outlet or, alternatively, the same as the inlet. The transfer element can be for example an image plate carriage, an adapter, or a cassette relevant to the imaging medium.

According to one embodiment, in communication with the image plate readout device is arranged a sensing element for detecting an object. In addition, the sensing element is set in data communication with the readout device, such that, upon detecting an object in the proximity of a readout device, the sensing element is adapted to deliver a signal to the readout device. Still further, the readout device, after being triggered by a signal delivered by the sensing element, is adapted to execute some function, for example to activate a receiver element encompassed by the readout device for receiving an image plate and/or a transfer element intended for the image plate.

Indeed, an image plate readout device of the foregoing type, equipped with sensing elements, offers distinctive benefits with respect to the prior art, for example a device operating in a non-contact manner or with minimal contact, whereby persons operating the readout device need not touch the readout device or its control instruments in the process of feeding an image plate or a transfer element into the readout device. An advantage provided by a non-contact or minimal contact procedure is in turn that the spreading of disease carriers, which have possibly ended up in the operators' hands, by way of the readout device's control instruments to other users and thereby further to image plates, their protection devices, and other patients, can be effectively minimized.

According to one embodiment, the readout device comprises both a non-active operating mode and an active operating mode, whereby, upon being triggered by a signal delivered by a sensing element, the readout device is adapted to proceed from the non-active operating mode to the active operating mode. The non-active operating mode can be for example an off condition, a rest condition, or a standby condition. In order to proceed from the off condition to the active operating mode, the monitoring element may be provided for example with a mechanical device, for example a mechanical switch. In view of proceeding from the rest or standby condition to the active operating mode, the monitoring element may be provided for example with a sensor observing its surroundings in a non-contacting manner.

According to one embodiment, the activation of a receiver element comprises activating an entrance to the readout device, for example opening a lid, for the insertion of an image plate, either as such or disposed within a transfer element, into said entrance. The activation of a receiver element may also comprise setting a gripper element encompassed by the readout device in a standby status for placing an image plate in said gripper element either as such or disposed within a transfer element. The gripper element can be constructed for example by means of a mechanical gripper mechanism and/or magnetically as well known for the skilled artisan.

According to one embodiment, setting the receiver element in an offering condition comprises leaving a read-out and/or cleaned image plate in the entrance of a readout device to be picked up by the operator, for example for a specific period of time. The readout device executes an offering condition as long as one or more of the following take place: the object stays in the proximity of a readout device longer than some preset time, the object returns to the proximity of a readout device within some preset time, and the object makes some gesture and/or motion within some preset time after the sensing device has detected the object. In the process of setting the receiver elements of a readout device in the offering condition, it is possible to utilize in a diverse manner for example the time that the object spends in the proximity of the readout device. It is possible, for example, to determine that, when the object spends some preset time, for example 2 seconds, alongside the device, the reading and cleaning of an image plate will be executed, and, if the object stays alongside the device for example 4 seconds, both the reading and cleaning, as well as the setting of receiver elements in the offering condition, will be executed. The readout device may also be adapted, for example, to execute the offering condition in case no function of the readout device has been otherwise prescribed for offering an image plate to the operator.

According to one embodiment, the conveyor mechanism is also adapted to become activated as triggered by a signal delivered by the sensing detector, and to execute the conveyance of an image plate within a readout device, for example the conveyance of an image plate through a readout device.

According to one embodiment, the readout device further comprises also guidelining elements for instructing the operator of a readout device, whereby the readout device, having been triggered by a signal delivered by the sensing element, is adapted to also activate said guidelining element and to supply said guidelining element with information instructing the operator.

According to one embodiment, the readout device, or one of its components or functions, does not activate until an object is detected for example in the proximity of a readout device by at least two separate sensing elements and until a signal is delivered to the readout device by both of these elements. The sensing elements can be sensing objects for example within various ranges from a readout device, and when an object moves for example from one outer range towards a closer range, a signal will be delivered, yet with a specific time interval, by both elements sensing objects within both the outer range and the closer range. From this can be concluded that the detected object, for example the operator of a readout device, is approaching the readout device and the activation can be executed. Said procedure enables the activation of functions, for example setting a readout device in the offering condition, as long as the procedure transpires within some preset time or after some preset time, to be achieved also by a specific gesture, for example by waving a hand in a certain way within the sensing ranges of a readout device's sensing element, by a specific time period spent by the object, for example a hand, within the sensing ranges of a readout device's sensing element, or by a combination of a specific gesture and its point in time.

According to one embodiment, the readout device, or one of its components or functions, does not activate until an object is detected for example in the proximity of a readout device by at least one sensing element and until a signal is delivered to the readout device by this element. The sensing element can be sensing objects for example within various ranges from a readout device, and when an object moves for example from one outer range towards a closer range, a signal will be delivered, yet with a specific time interval, by the sensing element sensing objects within both the outer range and the closer range. From this can be concluded that the detected object, for example the operator of a readout device, is approaching the readout device and the activation can be executed. In addition, the activation of functions can be executed, for example when the procedure transpires within some preset time or after some preset time, also by a specific gesture, for example by waving a hand in a certain way within the sensing ranges of a readout device's sensing element, by a specific time period spent by the object, for example a hand, within the sensing ranges of a readout device's sensing element, or by a combination of a specific gesture and its point in time.

According to one embodiment, the gestures made by an operator are observed by means of a radar or a camera, based for example on pattern recognition, and a procedure relevant to the detected gesture is executed, for example the receiver elements are activated, the image plate is read, the operator is instructed for example by supplying the guidelining element with user instruction information, the receiver elements are set in an offering condition, or an installation cleaning process is conducted for example by emitting electromagnetic radiation and/or ultrasonic radiation, destroying disease carriers, towards an object within the installation. A specific gesture may be matched by a specific procedure.

According to one embodiment, the sensing element may also recognize an operator for example on the basis of a user-related identifier, whereby the readout device can be adapted to execute certain actions relevant to this particular user. It is possible, for example, to identify a novice operator, in which case the readout device may supply the guidelining element with more detailed information. The sensing element may also identify the employed imaging medium and execute some relevant procedure, for example clean the conveyor mechanism in the event that the imaging medium is an intraoral image plate.

The sensing element can be implemented by any means well known for the skilled artisan, for example by means of an infrared sensor, a thermal sensor, an RFID sensor, a photocell, a laser rangefinder, a capacitive sensor and/or a resistive sensor, by means of a radar or a camera, or by means of a mechanical device. The mechanical device can be for example a mechanical switch, which is switched to a different condition by an image plate or a transfer element in the process of inserting the image plate or the transfer element for example into the entrance or the adapter of a readout device.

It should also be noted that, according to one embodiment for improving the hygiene of a readout device, the surfaces of a readout device, or elements encompassed thereby, can be coated with a so-called antimicrobiological material. According to one embodiment, a specific part of the readout device can also be manufactured from an antimicrobiological material. Such antimicrobiological material can be for example a material included in the SAME group (self-assembling monolayer end groups).

DESCRIPTION OF THE FIGURES

Preferred embodiments of the invention will be described in the next section in slightly more detail with reference to the accompanying FIGURES, in which.

MORE DETAILED DESCRIPTION OF THE FIGURES

Figure 1A:
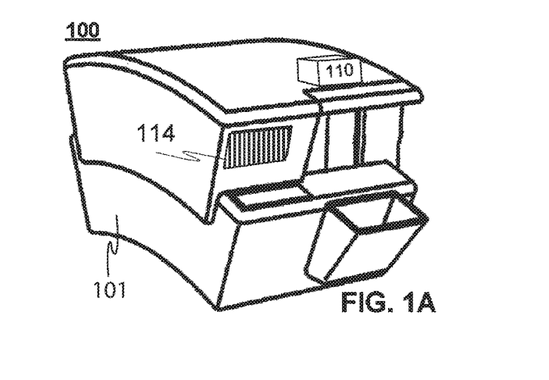
FIGS. 1A-1C show one exemplary image plate readout device and a sensing arrangement relevant thereto.
Figure 1B:
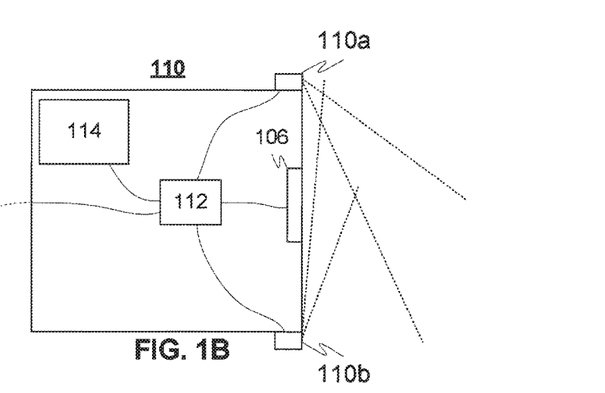
Figure 1C:
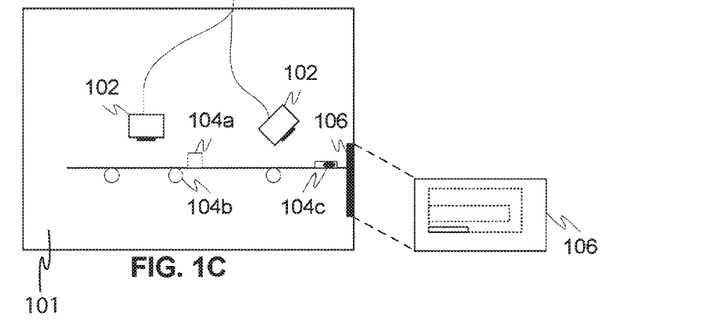

FIG. 1A shows one exemplary image plate readout device 100, FIG. 1B a sensing arrangement 110 associated with the readout device, and FIG. 1C conveyor mechanisms 104a, 104b, 104c and disinfecting elements 102 encompassed by the readout device. According to one embodiment, the sensing elements 110 are integrated with the readout device 100, but according to another embodiment, the sensing elements are linked with the readout device 100 and in data communication therewith. It should be noted that, without changing the underlying inventive idea, the sensing element or elements can be at a distance from a readout device and in connection with the readout device by way of some data communication link known for the skilled artisan, for example by way of a wired or wireless communication.

The exemplary sensing arrangement 110 shown in FIG. 1B comprises sensing elements 110a, 110b, which are set in data communication with a control unit 112 in such a way that, upon detecting an object for example in the proximity of a readout device, the sensing element is adapted to deliver a signal to the readout device's control unit 112. In addition, the sensing arrangement 110 is adapted to detect, with the readout device 100 being in an active operating mode, having switched thereto for example after detecting an object in its proximity, whether the object remains in the proximity of the readout device 100 for a time period longer than a preset time. For example, the operator of a readout device leaves his/her hand in the proximity of an entrance 106 to the readout device, in which case the sensing arrangement 110 delivers a signal to the control unit 112. On the other hand, the sensing arrangement 110 may be adapted to detect whether an object returns to the proximity of the readout device 100 within some preset time period after the sensing arrangement 110 has detected the object the previous time in the proximity of the readout device 100. On the other hand, the sensing arrangement 110 can also be adapted to detect some specific gesture and/or motion of an object, for example within some specific preset time frame, after the sensing arrangement 110 has detected the object in the proximity of the readout device 100 and the readout device 100 has proceeded to an active mode. The fulfillment of previously defined time conditions is monitored by the sensing arrangement 110 and/or by the control unit 112. Said control unit 112 is in turn adapted, having been triggered by a signal delivered by the sensing arrangement, to activate functions of the readout device and elements associated with the readout device, for example to activate a receiver element for the reception of an image plate and/or a transfer element. The activation of a receiver element may proceed for example by way of a data communication link between the receiver element and the control unit.

The readout device control unit 112 may activate for example a set of instruments relevant to the entrance 106 of a readout device for enabling the placement of an image plate in said entrance, either as such or disposed in a transfer element, for example the opening of a protective lid of the entrance. The control unit may also set the gripper element 104c in a standby condition for enabling the placement of an image plate in the gripper element, either as such or disposed in a transfer element, for example to push the gripper element 104c out of the entrance 106 for example in such a way that the image plate or the transfer element can be placed therein. In addition, the control unit 112 is able, upon receiving a message about the dwelling of an object in the proximity of the readout device 110, about the return of an object back to the proximity of the readout device 110 or about a specific gesture and/or motion of an object in the proximity of the readout device 110, for example to bring a set of instruments relevant to the readout device entrance to an offering condition in which a cleaned image plate is left in the readout device entrance 106 to be picked up, depending on whether the condition relevant to a preset time is fulfilled. Thus, the operator, who has inserted an image plate into the readout device 100, is able to pick up the cleaned image plate directly from the entrance 106 without passing the image plate to a collecting unit for cleaned image plates, included in the readout device 106 and visible in FIG. 1A at a front part of the readout device, which can be for example a collecting tray. Should a cleaned image plate not be picked up from the entrance 106, the readout device 110 is adapted to convey the image plate to a collecting unit for example after some prescribed delay or when the readout device 110 switches to a non-active mode. On the other hand, the readout device 110 may also be adapted to leave an image plate in the entrance to be picked up while switching to a non-active mode.

In addition, the readout device control unit 112 may also activate the conveyor mechanism 104*a*, 104*b* for bringing an image plate, either as such or disposed in a transfer element, to a position enabling its reading by the readout device's reader unit, for example after inserting the image plate into the receiver elements. According to one embodiment, the conveyor mechanism may also carry a transfer element alone without an image plate, for example in an embodiment in which it is desirable to disinfect just the transfer element.

Still furthermore, the readout device control unit 112 may also activate guidelining elements 114 for instructing the operator of a readout device and supply the guidelining element with user instruction information.

According to one embodiment, the control unit 112 does not activate a component, element, or function encompassed by the readout device until an object is detected and a signal is delivered to the readout device by at least two sensing elements 110*a*, 110*b*. The detection or sensing elements 110*a*, 110*b* can be disposed for example in such a way that the motion of an object from further away towards the readout device is detected thereby at different distances, the control unit 112 being able to conclude that the object is approaching the readout device, for example on the basis of time differences between signals delivered by various sensing elements.

According to one embodiment, the sensing element 110*a*, 110*b* can be a camera or a radar with an ability to detect gestures or motions performed by the operator, for example on the basis of pattern recognition. In this case, the control unit 112 is adapted to interpret the gestures or motions performed by the operator and to execute a procedure relevant to the detected gesture, for example to activate receiver elements, to read an image plate, to instruct an operator, to set receiver elements in an offering condition, or to execute an installation cleaning process, for example by using the disinfecting elements 102 to emit electromagnetic and/or ultrasonic radiation, destroying disease carriers, towards an object to be cleaned, for example towards the conveyor mechanisms 104*a*, 104*b*, 104*c* (gripper element) and/or the entrance or adapter 106 of a readout device. The control unit 112 is preferably set in data communication with the conveyor mechanisms and/or disinfecting elements 102 of a readout device.

Described above are but a few embodiments for a solution of the invention. The principle of the invention is naturally subject to variations within the scope of protection defined by the claims, regarding, for example, implementation details as well as application sectors. For example, there may be one or more or several types of sensing elements for detecting diverse objects and/or gestures.

It should also be noted that the equipment and instruments shown in the figures are not necessarily to scale in all aspects thereof, and that for example the image plates and/or the transfer elements encompassing an image plate can be fed into the readout device also in vertical plane, even though, for example in FIG. 1C, the adapter 106 is depicted in horizontal plane.

The invention claimed is:

1. A system for receiving and reading imaging media, the system comprising:
a readout device having a housing, and a reader unit in the housing, the reader unit configured to read an imaging medium within the housing;
a receiver element associated with the housing, the receiver element configured to receive into the housing at least one of the imaging medium and a transfer element for an imaging medium for subsequent reading by the reader unit;
a sensing element that detects a gesture or motion of an object of detection by a non-contacting manner; and
a control unit in communication with the sensing element, the control unit causing the readout device to execute a function when the sensing element detects the gesture or motion of the object of detection;
wherein the object of detection is a portion of a body of an operator of the readout device and the gesture or motion is performed by the operator using the portion of the body of the operator.

2. The system according to claim 1, wherein the gesture comprises at least one gesture of a circle, a line, or a figure drawn by the operator.

3. The system according to claim 1, wherein the gesture or motion comprises a presence of the object of detection in a location proximate to the readout device for a certain time.

4. The system according to claim 1, wherein the function comprises initiating an operating mode of the readout device.

5. The system according to claim 1, further comprising a plurality of sensing elements, the plurality of sensing elements including the sensing element, wherein the plurality of sensing elements detect a gesture or motion of an object of detection by a non-contacting manner, and wherein the control unit causes the readout device to execute a function when at least two of the sensing elements of the plurality detect the gesture or motion of the object of detection.

6. The system according to claim 1, further comprising at least one disinfecting element located within the readout device, wherein the function comprises activating the at least one disinfecting element to clean at least a portion of an interior of the readout device.

7. The system according to claim 1, wherein the sensing element comprises at least one camera.

8. The system according to claim 7, wherein the control unit receives image data from the camera and the object of detection is detected in the image data by the control unit using pattern recognition.

9. The system according to claim 1, wherein the sensing element comprises at least one sensor selected from infrared imaging, thermal imaging, radio frequency identification (RFID), photocell, laser rangefinder, capacitive sensing, and resistive sensing.

10. A method for receiving and reading image media, the method comprising:
sensing with a sensing element a presence of an object of detection located outside of a housing of a readout device and prior to receipt of at least one of an imaging medium and a transfer element for an imaging medium into the housing of the readout device by a receiver element;

detecting a motion of the object of detection in a proximity of the readout device; and operating a control unit to cause the readout device to execute a function when the sensing element senses the object of detection.

11. The method according to claim 10, wherein the object of detection comprises a gesture or motion performed by an operator of the readout device.

12. The method according to claim 10, wherein the object of detection comprises a presence of an object in a location proximate to the readout device for a certain time.

13. The method according to claim 10, wherein the function, when the sensing element senses the object of detection, comprises operating the receiver element to open an entrance of the housing to the readout device.

14. The method according to claim 10, wherein the function, when the sensing element senses the object of detection, comprises activating a device associated with the entrance of the readout device for inputting at least one of the imaging medium and transfer element into the readout device.

15. The method according to claim 10, wherein the function, when the sensing element senses the object of detection, comprises setting a device associated with an entrance of the readout device in an offering condition for allowing at least one of the imaging medium and transfer element to be retrieved from the entrance.

16. The method according to claim 10, wherein the function, when the sensing element senses the object of detection, comprises conveying at least one of the imaging medium and transfer element from the receiver element to a reader unit of the readout device.

17. The method according to claim 10, wherein the function, when the sensing element senses the object of detection, comprises activating a guidelining element to instruct an operator of the readout device.

18. The method according to claim 10, further comprising:

operating at least the receiver element of the readout device in a non-active operating mode;

upon detecting a motion of the object of detection in a proximity of the readout device, with the controller, operating at least the receiver element to an active operating mode to receive at least one of the imaging medium and the transfer element for the imaging medium with the receiver element.

19. The method according to claim 10, further comprising:

operating at least a portion of the readout device in a non-active operating mode;

upon detecting a motion of the object of detection in a proximity of the readout device producing a signal indicative thereof from the sensing element to the controller; and upon receiving the signal from the sensing element, the controller operates the portion of the readout device in an active operating mode.

20. The method according to claim 19, wherein the portion of the readout device comprises at least one of the following portions:

the receiver element operable to receive at least one of the imaging medium and the transfer element when in the active operating mode;

the receiver element operable to offer an imaging medium or a transfer element when in the active operating mode;

a reader unit operable to read image data from the imaging medium when in the active operating mode;

a guidelining element operable to instruct an operator of the readout device when in the active mode; and a disinfecting unit operable to emit disinfecting radiation within the readout device to clean at least a portion of the readout device when in the active operating mode.

21. The method according to claim 10, further comprising:

detecting a motion of the object of detection in a proximity of the readout device at a plurality of distances from the readout device by a non-contacting manner.

22. A system for receiving and reading imaging media, the system comprising:

a readout device having a housing, and a reader unit in the housing, the reader unit configured to read an imaging medium within the housing;

a receiver element associated with the housing, the receiver element configured to receive into the housing at least one of the imaging medium and a transfer element for an imaging medium for subsequent reading by the reader unit;

a sensing element that detects a gesture or motion of an object of detection by a non-contacting manner; and a control unit in communication with the sensing element, the control unit causing the readout device to execute a function when the sensing element detects the gesture or motion of the object of detection wherein the readout device comprises an entrance into the housing and comprises a device associated with the entrance of the readout device configured to engage at least one of the imaging medium and transfer element, and the function comprises setting the device associated with the entrance of the readout device in an offering condition for allowing at least one of the imaging medium and transfer element to be retrieved from the entrance.

23. A system for receiving and reading imaging media, the system comprising:

a readout device having a housing, and a reader unit in the housing, the reader unit configured to read an imaging medium within the housing;

a receiver element associated with the housing, the receiver element configured to receive into the housing at least one of the imaging medium and a transfer element for an imaging medium for subsequent reading by the reader unit;

a sensing element that detects a gesture or motion of an object of detection by a non-contacting manner; and a control unit in communication with the sensing element, the control unit causing the readout device to execute a function when the sensing element detects the gesture or motion of the object of detection;

wherein the readout device comprises a guidelining element for instructing an operator of the readout device, wherein the function comprises activating the guidelining element to instruct the operator.

24. A system for receiving and reading imaging media, the system comprising:

a readout device having a housing, and a reader unit in the housing, the reader unit configured to read an imaging medium within the housing;

a receiver element associated with the housing, the receiver element configured to receive into the housing at least one of the imaging medium and a transfer element for an imaging medium for subsequent reading by the reader unit;

a sensing element that detects a gesture or motion of an object of detection by a non-contacting manner;

a control unit in communication with the sensing element, the control unit causing the readout device to execute a function when the sensing element detects the gesture or motion of the object of detection; and a conveyor mechanism that conveys at least one of the imaging medium and transfer element in the readout device from the receiver element to the reader unit, wherein the function comprises conveying with the conveyor mechanism at least one of the imaging medium and transfer element from the receiver element to the reader unit.

25. The system according to claim 24, wherein the object of detection is a portion of a body of an operator of the readout device and the gesture or motion is performed by the operator using the portion of the body of the operator.

26. The system according to claim 24, wherein the object of detection is at least one of the imaging medium and the transfer element.

27. A system for receiving and reading image media, the system comprising:

a readout device having a housing, and a reader unit in the housing, the reader unit configured to read an imaging medium within the housing;

a receiver element associated with the housing, the receiver element configured to receive into the housing at least one of the imaging medium and a transfer element for an imaging medium for subsequent reading by the reader unit;

a sensing element that detects a gesture of motion of an object of detection by a non-contacting manner;

a control unit in communication with the sensing element, the control unit causing the readout device to execute a function when the sensing element detects the gesture or motion of the object of detection; and at least one disinfecting element located within the readout device, wherein the function comprises activating the at least one disinfecting element to clean at least a portion of an interior of the readout device.

* * * * *